United States Patent [19]

Holtkamp, Sr.

[11] Patent Number: Plant 7,684

[45] Date of Patent: Oct. 22, 1991

[54] AFRICAN VIOLET PLANT NAMED ROSE

[76] Inventor: Reinhold Holtkamp, Sr.,
Blumenstrasse 28, D 4242
Rees-Haffen, Fed. Rep. of Germany

[21] Appl. No.: 565,312

[22] Filed: Aug. 10, 1990

[51] Int. Cl.[5] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner

[57] ABSTRACT

A new and distinct cultivar of African violet named Rose characterized by its small, double pink flowers; strong, upright flower stems that curve slightly toward the center to form a compact bouquet above the leaves; large, dark green, oval to spear-shaped leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Rose.

The new cultivar was referred to during the breeding and selection process by the designation 906 L.M. rot rosa 50 and is a product of a planned breeding program. The new cultivar was originated from a cross made by me in the controlled breeding program in Haffen, Federal Republic of Germany. The female, or seed parent was a cultivar designated Arizona III. The male, or pollen parent was a cultivar designated 282.

Rose was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Rose has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Rose, which in combination distinguish this African violet as a new and distinct cultivar:

(1) Strong, upright flower stems curving slightly toward the center.

(2) Small, pink double flowers.

(3) Each plant carries 9–11 and more upright flower stems each of which carries 9–11 and more flowers.

(4) Long lasting, non-dropping flowers.

(5) Vigorous and compact grower.

(6) Plant saleable 10 to 11 weeks after potting.

(7) Seed capsules push slightly through.

(8) Large, dark green, oval to spear-shaped leaves.

(9) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Rose.

Parentage:

*Male parent.*—Arizona III.

*Female parent.*—282.

Propagation: The new cultivar holds its distinguishing characteristics through successive propagations by leaf cuttings.

Plant: From 9 cm to 12 cm tall when grown in pots, and approximately 25–28 cm in diameter when fully grown.

*Leaves.*—General form: Oval to spear-shaped. Diameter: 65–75 mm wide and 80–90 mm long. Texture: Leather-like. Aspect: Hairy, slightly shiny. Veins: Upperside: well visible; underside: well pronounced, light green, shiny. Color (upperside): Yellow-Green Group 147 A and darker. Color (underside): Greyed-Purple Group 186 B to C. Petiole: Strong upright, purplish brown hairy.

*Flowers.*—Buds: Ball-shaped, 6–7 mm just before opening, pink. Sepals: Five (5). Color: Purplish brown. Calyx: Shape: Almost flat. Aspect: Spear-shaped hairy. Peduncle: Character: Strong upright, hairy. Color: Green with purplish brown touch.

*Individual flowers.*—Size: 34–38 mm. Shape: Double. Color (upperside): Purple Group 78 covering all shades from A to D. Under cooler temperatures and more intensive lighting, the pink tends to intensify. Color (underside): Purple Group 78 B to D. Borne: Each flower stem carries 9–11 and more flowers on strong, upright peduncles that are free standing above the leaves, thereby forming a compact bouquet. Flowering habit: Flowers 10–11 weeks after potting.

Reproductive organs:

*Stamens.*—Two (2). Anthers: 2 composed of 4 anther cells, seed capsule pushes slightly through.

*Filaments.*—Yellowish green with pink touch, 3–4 mm long.

*Pollen color.*—Yellow Group 7 A.

*Styles.*—7–8 mm long, purplish red, base of ovary light green and hairy.

Roots: Normally developed, white when young, turning slightly brownish when older.

Disease resistance: Up to date, Rose has shown very good resistance to all major violet diseases.

General observations: Rose is very attractive due to a nice bouquet of small, double pink flowers. A tight cluster of flowers free standing above the leaves develops after approximately 10–11 weeks. Each of the 9–11 and more strong flower stems carries 9–11 and more flowers having different shades of pink. The anthers are usually covered up. The flowers are long-lasting and non-dropping and the seed capsules push slightly through. Rose is a vigorous and compact grower with large, dark green, oval to spear-shaped leaves.

I claim:

1. A new and distinct cultivar of African violet named Rose, as described and illustrated, and particularly characterized by its small, double pink flowers; strong, upright flower stems that curve slightly toward the center to form a compact bouquet above the leaves; large, dark green, oval to spear-shaped leaves; profuse flowering, vigorous and compact growth habit, flowering 10–11 weeks after potting, and its long lasting and non-dropping flowers.

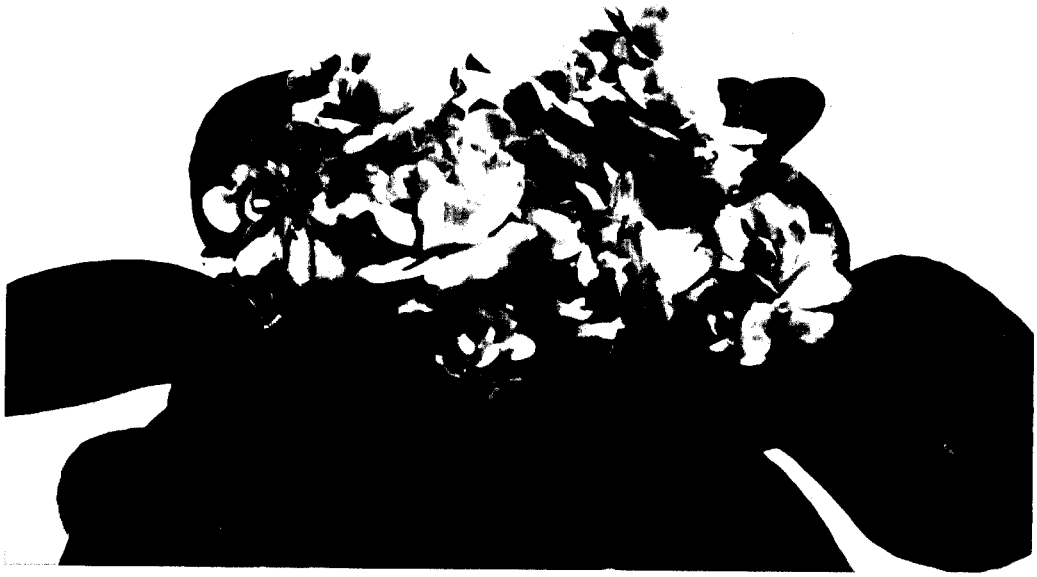

* * * * *